United States Patent
Opitz et al.

(10) Patent No.: US 8,007,169 B2
(45) Date of Patent: Aug. 30, 2011

(54) SENSOR

(75) Inventors: Bernhard Opitz, Leonberg (DE); Ando Feyh, Tamm (DE); Daniel Herrmann, Tuebingen (DE); Oliver Wolst, Nuertingen (DE)

(73) Assignee: Robert Bosch GmbH, Stuttgart (DE)

( * ) Notice: Subject to any disclaimer, the term of this patent is extended or adjusted under 35 U.S.C. 154(b) by 323 days.

(21) Appl. No.: 11/921,669

(22) PCT Filed: Jun. 13, 2006

(86) PCT No.: PCT/EP2006/063152
§ 371 (c)(1),
(2), (4) Date: Jan. 6, 2009

(87) PCT Pub. No.: WO2007/054380
PCT Pub. Date: May 18, 2007

(65) Prior Publication Data
US 2009/0129440 A1  May 21, 2009

(30) Foreign Application Priority Data
Jul. 6, 2005 (DE) .................. 10 2005 031 604

(51) Int. Cl.
G01K 7/00 (2006.01)
(52) U.S. Cl. .............. 374/178; 374/183; 374/185
(58) Field of Classification Search .......... 374/178, 374/183, 185
See application file for complete search history.

(56) References Cited

U.S. PATENT DOCUMENTS
5,600,174 A    2/1997    Reay et al.
2004/0169579 A1  9/2004  Mattes et al.

FOREIGN PATENT DOCUMENTS
DE    19845112       4/2000
DE    10219247       12/2003
DE    102004024285   12/2005

OTHER PUBLICATIONS

Translation of DE 10219247.*
International Search Report, PCT International Patent Application No. PCT/EP2006/063152, dated Oct. 2, 2006.
Nassiopoulou AG et al.: "Porous Silicon as an Effective Material for Thermal Isolation on Bulk Crystalline Silicon" Physica status solidi (A). Applied Research, Berlin, DE, vol. 182, No. 1, Mar. 12, 2000, pp. 307-311, XP008001587.

* cited by examiner

Primary Examiner — Lisa M Caputo
Assistant Examiner — Mirellys Jagan
(74) Attorney, Agent, or Firm — Kenyon & Kenyon LLP

(57) ABSTRACT

A sensor, in particular a thermal sensor and/or gas sensor, encompassing an electrical sensor component having an electrical property whose value changes in temperature-dependent fashion, wherein the temperature-dependent electrical property is a resistance or an impedance. Thermal and electrical decoupling of the active structure from the substrate is accomplished by way of porous silicon and/or a cavity manufactured by electropolishing.

14 Claims, 5 Drawing Sheets

Fig. 9A Fig. 9B

SENSOR

FIELD OF THE INVENTION

The present invention relates to a sensor, in particular a thermal sensor and/or gas sensor, and to a method for manufacturing said sensor.

BACKGROUND INFORMATION

Conventionally, thermal sensors may be implemented using thin-layer technology, with the aid of temperature-dependent resistors, by preference Pt resistors, or with the aid of thermopiles, which are structures for utilizing the thermal voltage at transitions between two different metals or between metal and polysilicon. For this, these structures are applied onto a thin dielectric membrane whose low thermal conductivity allows, for example, changes in a temperature profile across said membrane to be sensed. This principle is applied, for example, in air mass sensors.

Because of their manufacturing process, both embodiments exhibit a high susceptibility to drift and therefore have the disadvantage that they must be very laboriously stabilized, since the changes in material properties over the service life bring about a drift of the sensor element. Even with such stabilization (e.g., tempering processes), this drift can in some cases still be enormous.

The temperature profile is set by way of thin-layer structures, e.g., resistance heaters made of platinum. Membrane manufacture is usually effected using a bulk micromechanical (BMM) process, i.e., all the material except for the membrane must be removed from the back side of the substrate by anisotropic etching, e.g., using KOH (potassium hydroxide). For example, in one conventional manufacturing process a 1-µm thick silicon membrane is generated on a wafer having a layer thickness of 360 µm, by way of an etching process, by removing 359 µm of the silicon layer.

Thermal sensors are additionally used, for example, in fingerprint sensors. Here the special sensor structures, heaters, sensing elements, and the like are applied onto a bulk substrate having low thermal conductivity and comparatively stable mechanical properties, e.g., ceramics, since the mechanical load in this application is considerably greater. The heat flux through the skin ridges is then detected and analyzed in spatially dependent fashion.

Thermally decoupled membranes are moreover also of interest in the field of gas sensing. Semiconductor-based gas sensors are typically based on an adsorption-related change in the resistance of metal oxide layers, or on a change in the potential of functional gate layer stacks of field effect transistors. To ensure effective dissociation of adsorbates and sufficiently short response times, however, and at the same time to prevent permanent contamination, these sensors must be operated at elevated temperatures, typically T>150° C. Depending on the application, membranes manufactured using complex process steps must also be used for thermal decoupling, in order, when necessary, to minimize heat output or enable rapidly pulsed operation. A method for manufacturing such a membrane is described, for example, in German Patent Application DE 102 00 40 24 285.2, "Microstructured component and method for the manufacture thereof."

A further disadvantage of conventional systems results from their construction. Either high sensitivity or high mechanical stability can be achieved. With conventional methods, the two properties cannot be implemented simultaneously. A comparatively coarse spatial resolution, resulting from large planar structures of the thermopiles, Pt heaters, and sensor elements, may be disadvantageous.

SUMMARY

An object of the present invention to improve a sensor of the kind set forth above.

The present invention relates to a sensor which comprises a sensor element exhibiting a temperature-dependent electrical property in the form of a resistance or an impedance. A flow voltage $U_F$, produced by the electrical current flowing through the sensor component and dropping at said component, can thereby be generated. In a preferred example embodiment, the current through the component can be impressed on the component by a current source, in particular a constant current source. An alternating current source can, however, also be provided in order to supply power to a capacitive sensor element.

If the temperature dependence of the resistance or impedance, and therefore the voltage dropping at it, is known, a statement can therefore be made regarding the temperature existing at the sensor component. Components having linear characteristic curves, in particular having such curves that rise comparatively steeply, are particularly advantageous for such applications. The steeper and more linear these characteristic curves are, the more exact the statement regarding the temperature existing at the component or a temperature difference that is to be ascertained.

Semiconductor components are regarded as particularly suitable for constituting such a component, the flow voltage $U_F$ preferably being sensed at a p-n transition of the semiconductor component.

This procedure is based on the knowledge that the temperature-dependent flow voltage of a p-n transition is dependent only on the band gap of the semiconductor that is used, and not on its doping concentration. For silicon, this voltage is $dU_F/dT=-2$ mV/K. Other semiconductors are, however, also suitable in principle for constituting a sensor according to the present invention, for example germanium, SiGe, GaN, SiC, and other similar ones.

In order to raise the sensitivity of the sensor thus constituted, a voltage elevation can furthermore be provided by way of a series circuit of such components.

It may furthermore be advantageous, in order to reduce interference, to constitute the electrical contacts of the component directly on the p-type region and n-type region, respectively, of the p-n transition. A pickoff of the measured signal embodied in this fashion allows elimination of a further negative influence, resulting from lead resistance and contact resistance.

For applications in which it is desired to influence the ambient temperature in a region of the sensor, the latter can furthermore encompass a heating element. The capabilities of such a sensor are even further enhanced with an additionally constituted component that senses a reference temperature, and/or by the constitution of a gas-sensitive element.

For a resistive sensor principle, electrodes (typically Pt electrodes) can be applied. These serve to detect changes in resistance due to adsorption of gases in a functional layer (typically metal oxide) located thereabove. On the other hand, gas-sensitive field effect transistors (FETs) can also be implemented using the CMOS process. The gate functional layer typically contains an oxide layer and catalytic metal. Diodes or FETs, for example, can be provided as a heating system.

By disposing such sensor elements on a thermal insulation element, it is moreover possible to achieve a reduction in the temperature dependence of such active components with respect to a base element that supports them. An essential part of the invention is the use of porous silicon. A thermal insulation element of this kind therefore by preference has a porous structure that possesses not only positive thermal properties but also high stability. Porous silicon also produces an electrical decoupling from the substrate (specific resistance of porous silicon is typically approximately $10^6$ ohm/centimeter). As a result, many individual different sensor elements as described above can be put in place over a large area, in order to make available a sensor that is sensitive in terms of signal acquisition but very robust in terms of mechanical stability. The individual sensor elements can each be disposed on or in an additionally constituted insulation element or else on one insulation element used in shared fashion, which element in turn is constituted in a process step subsequent to the constitution of one of the aforesaid sensor elements.

In a further embodiment, an additional carrier layer can be applied over the structural configuration previously described, which layer covers at least individual, but by preference several or even all sensor elements. After coverage of the desired surface regions, the porous silicon serving in the previous embodiments as a thermal insulation element can be partially or even completely removed through correspondingly configured openings. Etching operations are particularly well suited for this, for example wet-chemical etching using KOH, $H_2O_2$ with HF, or dry etching processes such as $ClF_3$. If the porous silicon beneath the sensor element is completely removed, the latter is then suspended only on the carrier layer disposed above it, which for purposes of the invention is also referred to as a membrane since, upon complete removal of the porous silicon, it spans in supporting fashion the cavity thereby created.

Complete removal of the porous silicon means that temperature coupling from the substrate into the sensor element is now possible only via the medium present in the cavity thus constituted, and via the carrier layer or membrane. For further reduction of thermal coupling, a patterning of the carrier layer or membrane is proposed. This can be implemented, for example, by way of recesses bordering the respective sensor element. In this case the sensor element is suspended from individual connecting points of the carrier layer or membrane that constitute the mechanical connection to the substrate. The carrier layer or membrane in turn is preferably made of a thermally highly insulating material so that it itself exerts as little influence as possible on thermal inputs.

A further advantage may be achieved as a result of the small dimension of the diode structures, and the high spatial resolution resulting therefrom.

BRIEF DESCRIPTION OF THE DRAWINGS

FIGS. 9 and 9B show a measurement circuit configuration modified with respect to that of FIG. 7.

FIG. 9A is a plan view of the contacts of the circuit according to FIG. 7, corresponding to the depiction of the embodiment in 9B and 9 modified with respect thereto.

DETAILED DESCRIPTION OF EXAMPLE EMBODIMENTS

Figure 1:
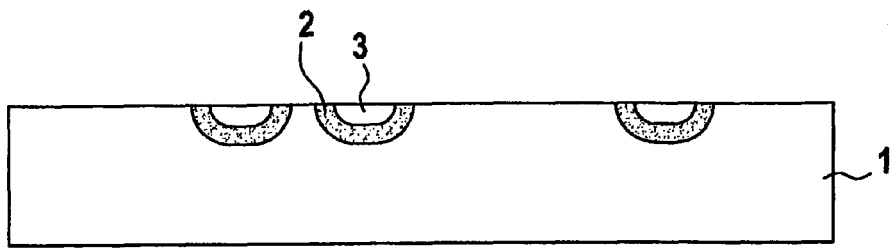
FIGS. 1 to 5 are schematic sectioned depictions through a semiconductor carrier at various steps of an example manufacturing process.

In detail, FIG. 1 shows a semiconductor carrier 1, made by preference of p-doped (100) silicon. Diode structures 2, 3 are constituted therein with the aid of standard semiconductor processes (implantation or diffusion). A p-type region 3 is introduced into an n-type zone 2. These are located on the one hand in region 6 of the thermally insulating well 4, and adjacent thereto in bulk region 7 (FIGS. 2-5). Region 4 is generated only in a later process step, and is drawn in FIG. 2 simply for better clarity. Diode 7 serves to measure the temperature reference (chip temperature), while diode 5 serves as a temperature sensor and diode 6 as a heater. For better thermal coupling, diodes 5 and 6 can also be implemented in an n-type well (cf. FIG. 10).

Once the diode structures have been completed, a thermal oxidation 8 (FIGS. 3-8) occurs, and a patterning of the oxide. The oxide film serves substantially to protect the p-n transition. It is preferably formed during the diffusion step of the implanted (diode) structures.

A masking layer 9 for the subsequent porous silicon process step is then applied and patterned. This layer serves to define the region of thermal insulation well 4 and to protect thermal oxidation layer 8 over the p-n transitions of the diode structures. Suitable as masking layer 9 here are layers that exhibit a low etching rate in hydrofluoric acid, in particular SiN, $Si_3N_4$, SiC. The layer thicknesses are typically in the range from 10 to 200 nanometers. This mask can, however, also be implemented by local n-type doping.

Figure 4:
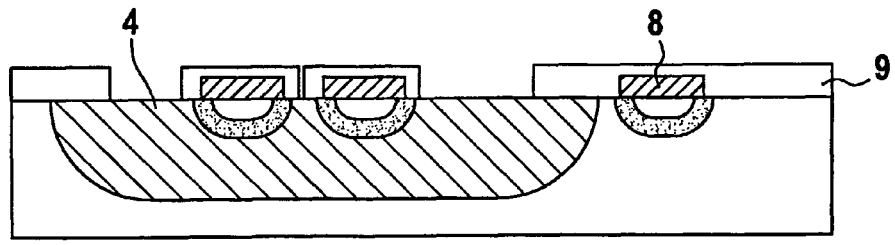
Figure 5:
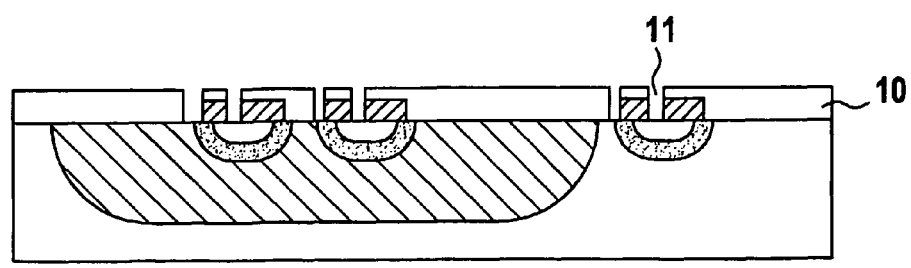
Figure 6:
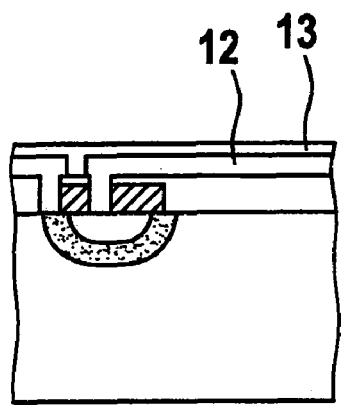
FIG. 6 shows a portion of such a semiconductor carrier after a later process step.

Thermal insulation well 4 is then generated (FIG. 4). For this, the silicon in the well region is porosified. This is done by electrochemical etching in an electrolyte containing hydrofluoric acid (HF). A wetting agent, which is by preference isopropanol, ethanol, or a surfactant, is added in order to reduce the surface tension. Depending on the substrate doping and the desired microstructure, the concentration in this context can be in the range between 10% and 50% HF. The porosity and therefore the thermal conductivity can be adjusted within wide limits (10%-80%) by selecting the current density.

Figure 2:
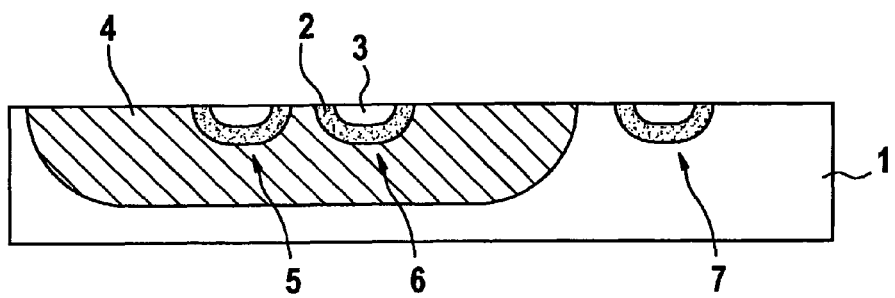
Figure 3:
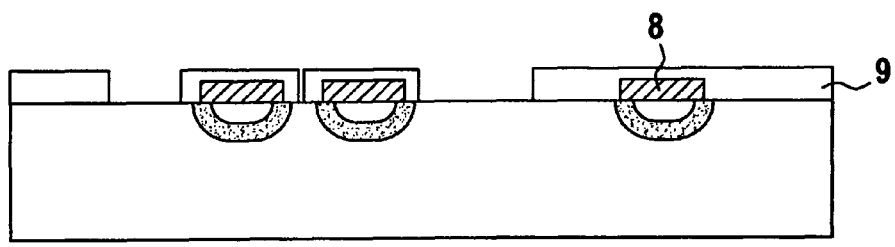

In order to ensure electrical functionality, it is important that the diode structures not be porosified. The present invention makes use in this context of the extreme doping selectivity of the porous silicon process. The diode structures introduced in the preceding process step are implemented via n-type wells (FIGS. 1-2) having p-type regions (FIGS. 1-3). The external n-type well is not attacked by the electrochemical process because holes (defect electrons) are necessary for the dissolution process of silicon; said holes are available in sufficient form in p-type silicon, but not in n-type Si. The functional structures are therefore inert with respect to the porous silicon process step.

Depending on the process parameters selected, it is thus possible to implement nanoporous, mesoporous, or macroporous structures. Nanoporous and mesoporous silicon is preferably used in order to achieve good thermal insulation. Macroporous silicon can also be advantageous, however, depending on the application.

Nanoporous silicon can be produced, by preference, at substrate doping levels below $10^{17}/cm^3$ and HF concentrations above 30%. Mesoporous silicon, on the other hand, is obtained with substrate doping levels above $10^{17}/cm^3$ and HF concentrations in the range of 10-40%.

For low thermal conductivity, the porosity should be greater than 50% if possible. Depending on the microstructure and porosity, thermal conductivity values in the range of 0.1-0.8 W/mK (bulk Si=156 W/mK) are achievable with this process. Porosities in the range of 50-70% are advantageous for high mechanical stability (utilization as an air mass sensor or fingerprint sensor). The best properties in terms of a combination of high mechanical stability and good thermal insulation exist when nanoporous silicon is used. This modification furthermore possesses extremely isotropic properties, which is advantageous for a fast thermal sensor.

The depth of insulation well 4 is by preference in the range of a few tens of µm to 100 µm; this requires between 5 minutes and 20 minutes depending on the etching rate. Because the etching process is highly isotropic, the inert diode structures are thus, as indicated in FIG. 4, completely underetched and are then embedded in porous material.

The isotropy of the etching process also results, among other effects, in an underetching of the mask (sketched in FIG. 4), but this can be taken into account in the membrane design.

Depending on the microstructure used for the porous silicon, an oxidation step can then be performed in order to stabilize the layer and further reduce thermal conductivity by partial oxidation. This is advantageous especially in the case of mesoporous silicon. Here the degree of oxidation is by preference 10-30%.

The p-n transitions are not influenced by this oxidation step, since temperatures only in the region around 400° C. are necessary to oxidize porous silicon because of its large internal surface area.

Etching mask 9 is then removed. It must be noted in this context that the etching mask needs to be etched selectively with respect to thermal oxide layer 8. This can be done either by wet chemistry, e.g., hot phosphoric acid when $Si_3N_4$/SiN is used, or physically. In the case of physical removal, however, a step is obtained in the well region, and it is also necessary to ensure that thermal oxide is still present over the p-n transitions after removal. A wet-chemical method is therefore generally preferable.

Depending on the application, however, the etching mask can also be left on the structure. An additional step of a few tens of nanometers is thereby raised. At the same time, process management is greatly simplified if the etching mask is not removed.

After deposition of a thin dielectric sealing layer (FIGS. 5-10) of 20-200 nm, by preference PECVD oxide, terminal contacts 11 of the diode structures are patterned. The electrical connections are produced by way of a metal layer (FIGS. 6-12), Al or AlSiCu preferably being used here. This ensures low-impedance resistive contacts. Lastly, a thin cover layer 13 on the order of 200 nm is deposited (SiN/$Si_3N_4$/SiC/$SiO_2$).

This process is also possible in principle using p-n-reversed dopings, but because back-side illumination is necessary during the porous silicon step in order to generate the necessary holes, this process is more complex.

When implementing resistive gas sensors, an electrode structure, preferably a Pt interdigital structure, can be applied onto the dielectric sealing layer (PECVD oxide) in the region of the diode or transistor structures for heating and for temperature measurement, and the sensitive layer (preferably made of a metal oxide) is then applied after porosification, optionally using thick- or thin-layer technology.

For the case of gas-sensitive field effect transistors, FETs and further requisite components can be patterned by suitable implantation before porosification of the thermal insulation well. CMOS processing is advisable when silicon is the semiconductor material. The active structures (FETs, optionally diodes, resistors) are implemented in an n-doped epitaxic layer. The latter protects the active elements in the subsequent porosification step. Extended p-type sinks permit porosification of the surrounding and underlying membrane region.

Once porosification is complete, the gate regions can be exposed and functional layer stacks can be processed. This functionalization also encompasses, in addition to thermal treatments, oxidation, and nitriding, a deposition of active materials such as, for example, oxides, oxide/nitrides, silicides, nitrides, or catalytic metals (e.g., Pt, Pd, Rh, Ir, Au) to assist in the dissociation of adsorbates. Sandwich structures and porous or patterned metallizations are also possible in this context.

The sealing layer on the porous silicon, and electrical contacting, can be effected as described above for the thermal sensors.

Electrical Configuration and Operation

Figure 7:
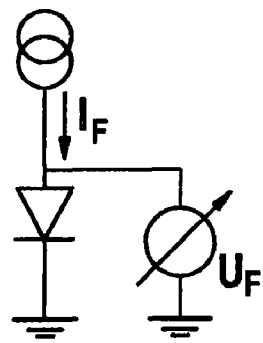
FIG. 7 shows an electrical measurement circuit.

The diodes for temperature measurement are operated in a constant-current mode (FIG. 7). A current source impresses a constant operating current $I_F$ of typically a few tens of µA. The voltage drop $U_F$ across the diode (flow voltage) is temperature-dependent, corresponding to the equation $$dU_F/dT = -2\text{mV/K(Si diode)}.$$

This correlation is independent of doping. It is defined only by the band gap of the semiconductor that is used (1.1 eV for Si).

For a mass flow sensor, in particular an air mass sensor, a heating element is additionally provided in order to implement a certain overtemperature and a temperature profile above the membrane. Ideally, this is once again done by way of a diode.

Figure 8:
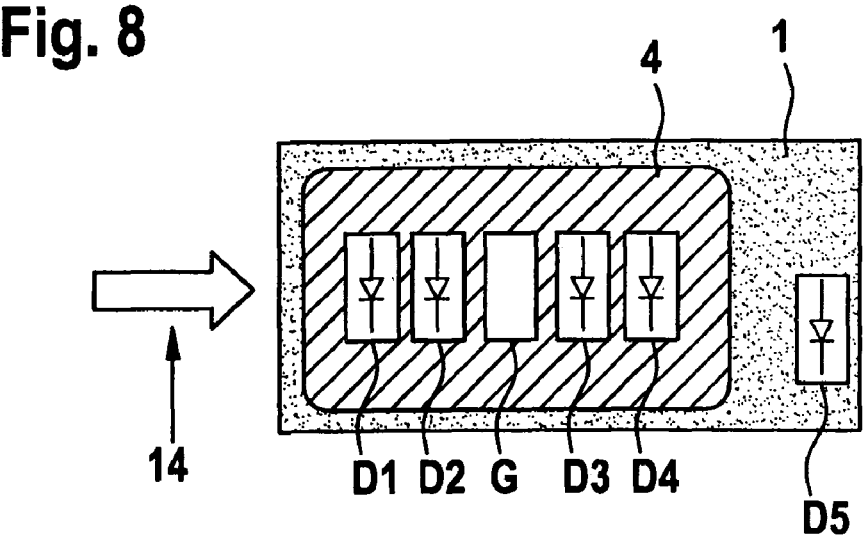
FIG. 8 is a plan view of a schematically depicted sensor assembly based on a semiconductor carrier according to FIGS. 1 to 6.
Figure 9:
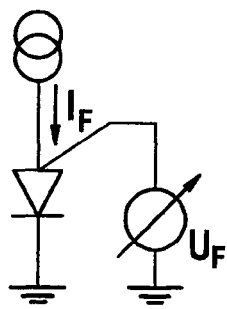
Figure 9:
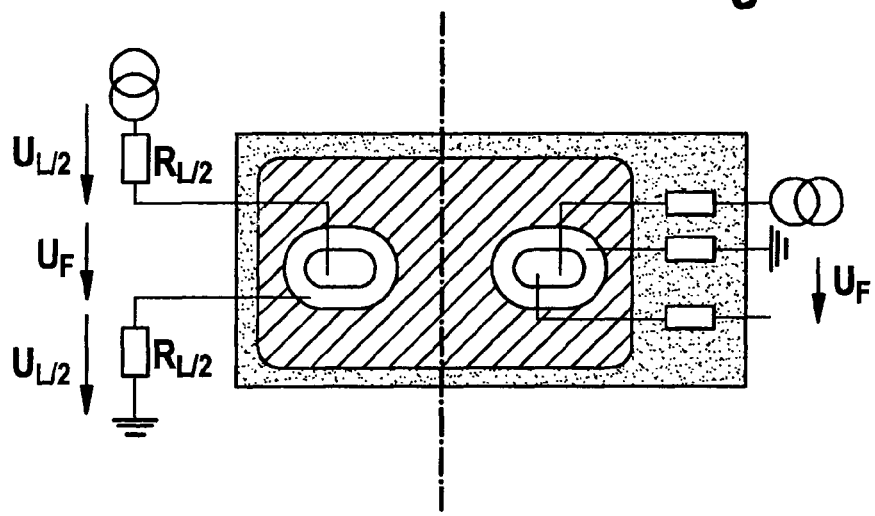

FIG. 8 schematically shows, in a plan view, a disposition of the diodes for an application as a mass flow sensor. Element G is not needed for this and is depicted only for illustrative purposes.

Diode D5 on substrate 1 serves to measure the chip temperature (reference). The flow direction of the medium to be sensed (e.g., air) is indicated by arrow 14.

The further sensor structures are implemented by way of diodes D1-D4 in well 4. Diodes D1 and D4 serve for temperature measurement, while diodes D2 and D3 function as heater diodes. Control is applied by establishing a constant overtemperature of D1 with respect to D5 using D2, and of D4 with respect to D5 using D3.

The mass flow can be sensed by measuring the difference in output of D2 and D3, measuring the respective diode current, and measuring the flow voltage across D1 and D4, since the mass flow changes the temperature profile established by D2 and D3 across the membrane.

Because, in the circuit proposed in FIG. 7, the measured signal is made up of the sum of the temperature-dependent voltage drop at diode $U_F$ and the lead and contact resistances $R_L$ ($U_M = U_F + U_L$) (FIG. 9A), a modified configuration (FIG. 9B) may be advantageous. The voltage can be measured in almost currentless fashion with the aid of a second pickoff directly at the anode. The voltage drop at leads and contacts therefore tends toward zero, and the accuracy of the method can thereby be greatly increased. There is, however, also an increase in the number of terminals required (e.g., bonding pads).

Figure 10:
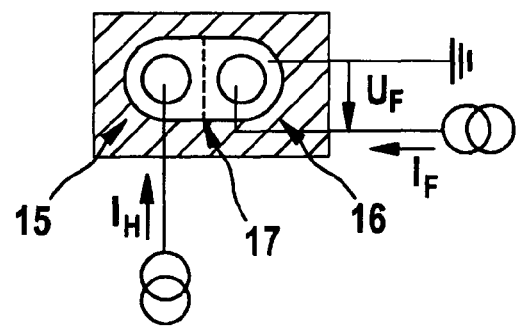
FIG. 10 shows a further modified embodiment of a measurement circuit.

In addition, measurement diode 16 and heating diode 15 can be implemented in a common n-type well (FIG. 10). The advantage of this variant is better thermal coupling of the measurement diode and heater diode. If applicable, a barrier 17 is also introduced in order to prevent electrical coupling of the measurement and heater diodes.

A further advantageous variant is represented by an implementation using transistors. The transistors for measuring temperature are constructed in the form of a so-called "band gap reference" circuit, thereby permitting a highly accurate temperature measurement.

The difference between the base-emitter voltages of two similar transistors A and B is utilized for this purpose. This difference is temperature-dependent and can be represented as $$\Delta U_{BE} = k_B T/e * \ln(I_A/I_B * A_B/A_A),$$

where e=elementary charge, $k_B$=Boltzmann's constant, T=temperature [K], $I_{A/B}$=current flow through transistors (it is preferable to use transistors with high current gain, for which $I_{A/B}=I_{CE,A/B}$), and $A_{A/B}$=electrically effective base cross section.

What is exploited here is the fact that the saturation current density $J_S$ of a transistor is only material-dependent. The current density through a transistor is therefore described by $$J_{A/B} = J_S \exp(e * U_{BE,A/B}/(k_B T)).$$

The use of transistors also offers advantages in terms of heating, permitting a higher power dissipation than diodes for the same heater current.

The $U_F(T)$ characteristic can also, if applicable, be stored in a characteristics diagram. This is a good choice if nonlinearities occur as a result of the layout.

Figure 11:
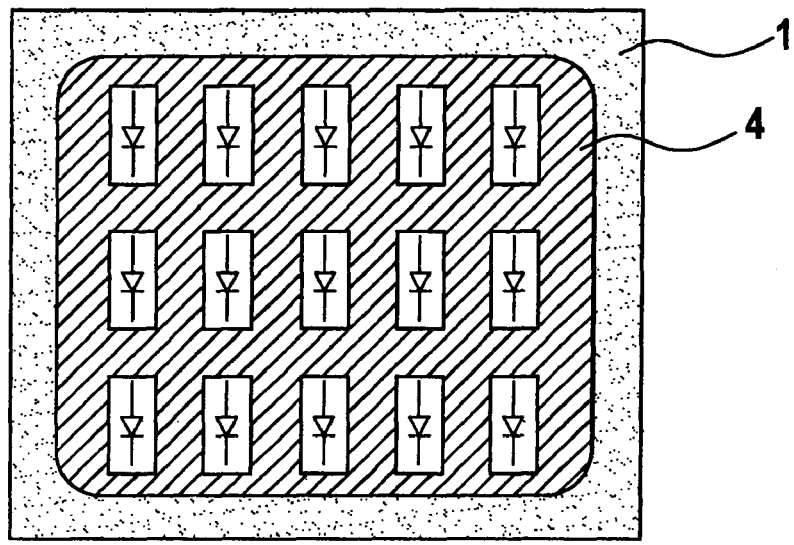
FIG. 11 is a plan view of a disposition of multiple sensitive elements on an insulation element used in shared fashion.
Figure 12:
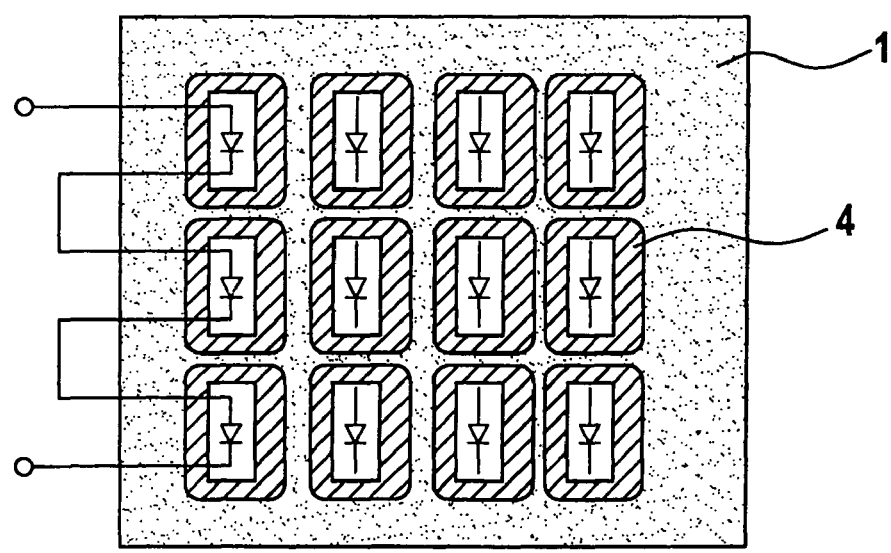
FIG. 12 is an embodiment modified with respect thereto and having separately constituted insulation elements, as well as a further modified embodiment of a sensor circuit.

Possible two-dimensional dispositions of the diode structures for position-sensitive sensing are depicted in FIGS. 11 and 12. FIG. 11 shows a disposition in one shared thermal insulation well. FIG. 12 shows a disposition in insulated individual well regions. In the case of FIG. 12, the individual units are thermally decoupled. The diode structures can be heaters, temperature sensors, or a combination of heaters and sensors.

In a further advantageous embodiment, a cavity can be generated beneath the porous silicon structure for better thermal decoupling. This can occur, for example, in the same process step by increasing the electrical current density (=electropolishing).

Figure 13:
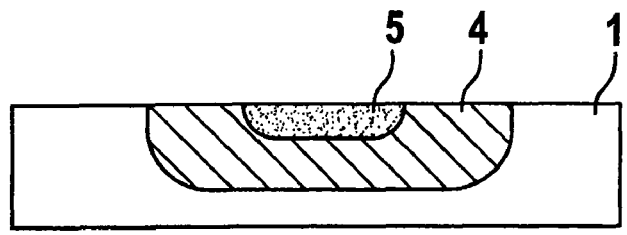
FIGS. 13 to 15 are schematic sectioned depictions of a further embodiment at various steps of a manufacturing process.
Figure 14:
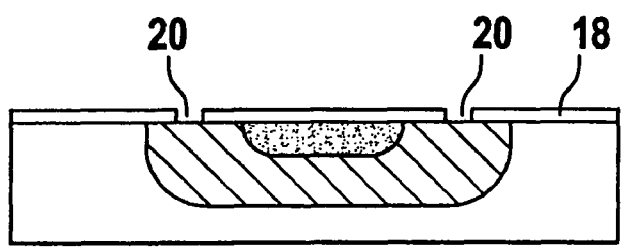
Figure 15:
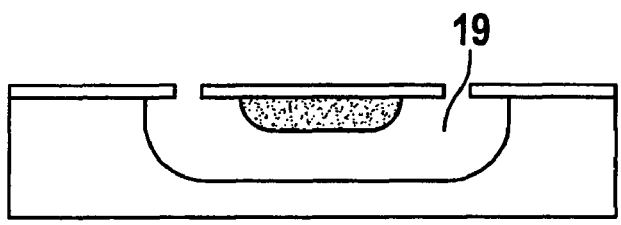
Figure 16:
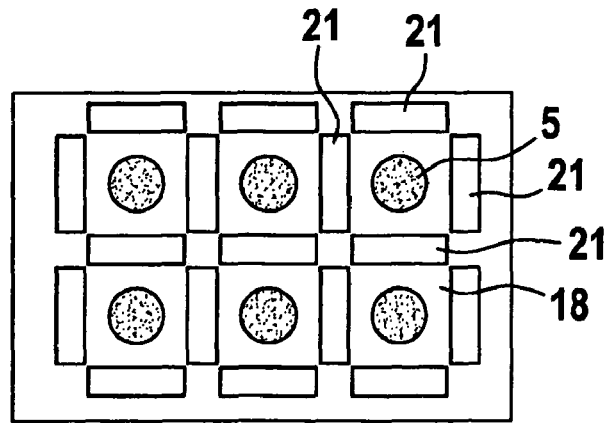
FIG. 16 is a plan view of this modified embodiment.

FIGS. 13 to 16 show an example embodiment of a sensor that has been further optimized in terms of thermal decoupling of individual sensor elements. To illustrate the process, only the surroundings of a single sensor are depicted in FIGS. 13 to 15. The plan view in FIG. 16 shows an example embodiment in which a group of sensors is correspondingly combined.

FIG. 13 shows, in detail, substrate 1 in which a previously described porous silicon, functioning as thermal insulation element 4, is embedded in the form of a well, and in turn receives the relevant sensor element, likewise in embedded fashion.

FIG. 14 shows a carrier layer or membrane 18, applied over the assembly of FIG. 13 and having two openings 20 constituted therein. Through these openings 20 the porous silicon constituted therebeneath can be removed as depicted in FIG. 15, for example by way of an etching method, in order to improve the thermal decoupling of the relevant sensor element. The thermal decoupling of the sensor element from the substrate via the carrier layer or membrane 18 can likewise be very positively influenced by configuring the membrane from a thermally highly insulating material.

A further positive influence on thermal decoupling is possible by additionally constituting corresponding structures 21 on membrane 18. For this purpose, in the example of FIG. 16, the respective sensor element is depicted, by way of example, bordered by approximately rectangular elongated recesses. Mechanically supporting connection is implemented via the individual corner points of the remaining membrane surfaces, by way of which, for example, the corresponding connections to the sensor elements can also be guided.

What is claimed is:

1. A sensor, comprising:
    an electrical sensor component having an electrical property whose value changes in temperature-dependent fashion;
    a heating element, the sensor component and the heating element being situated in a common n-type well; and
    an electrical coupling barrier between the sensor component and the heating element in the common n-type well;
    wherein the temperature-dependent electrical property is a resistance or an impedance; and
    wherein each of the sensor component and the heating element is a diode.

2. The sensor as recited in claim 1, wherein the sensor is at least one of a thermal sensor and a gas sensor.

3. The sensor as recited in claim 1, wherein the sensor component is a semiconductor component.

4. The sensor as recited in claim 1, wherein a series circuit of sensor components is provided.

5. The sensor as recited in claim 1, further comprising:
    a sensor component adapted to sense a reference temperature.

6. The sensor as recited in claim 1, further comprising:
    a gas-sensitive element.

7. The sensor as recited in claim 1, wherein the sensor component includes a p-n transition.

8. The sensor as recited in claim 7, wherein electrical contacts of the sensor component are constituted directly on a p-type region and an n-type region of the p-n transition.

9. The sensor as recited in claim 1, wherein the sensor component is disposed in or on a thermal insulation element.

10. The sensor as recited in claim 9, wherein the thermal insulation element has a porous structure.

11. The sensor as recited in claim 9, wherein the thermal insulation element is embodied as a carrier membrane.

12. The sensor as recited in claim 11, wherein the carrier membrane spans a cavity in which the sensor component is arranged.

13. The sensor as recited in claim 11, wherein the carrier membrane exhibits a patterned structure.

14. A method for manufacturing a sensor, the sensor including an electrical sensor component having an electrical property whose value changes in temperature-dependent fashion, a heating element, wherein each of the sensor component and the heating element is a diode, the sensor component and the heating element being situated in a common n-type well, and an electrical coupling barrier situated between the sensor component and the heating element in the common n-type well, the method comprising:
    forming the electrical sensor component; and
    after the forming of the electrical sensor component, forming an insulation element that thermally insulates at least the sensor component.

* * * * *